United States Patent [19]
Benoit et al.

[11] Patent Number: 5,866,551
[45] Date of Patent: Feb. 2, 1999

[54] RECOMBINANT ADERO VIRUSES COMPRISING AN INSERTED GENE ENCODING APOLIPOPROTEIN AND THEIR USE IN GENE THERAPY FOR DYSLIPOPROTEINEMIAS

[75] Inventors: Patrick Benoit, Paris; Patrice Denefle, Saint Maur; Michel Perricaudet, Ecrosnes; Sandrine Seguret, Montigny Le Bretonneux; Emmanuelle Vigne, Ivry Sur Seine, all of France

[73] Assignee: Rhone-Poulenc Rorer S.A., Antony Cedex, France

[21] Appl. No.: 535,243

[22] PCT Filed: Apr. 15, 1994

[86] PCT No.: PCT/FR94/00422

§ 371 Date: Jan. 11, 1996

§ 102(e) Date: Jan. 11, 1996

[87] PCT Pub. No.: WO94/25073

PCT Pub. Date: Nov. 10, 1994

[30] Foreign Application Priority Data

Apr. 30, 1993 [FR] France ................................. 93/05125

[51] Int. Cl.$^6$ .............................. C12N 15/63; C12N 5/00; A01N 43/04; A61K 31/70
[52] U.S. Cl. .......................... 514/44; 435/320.1; 435/455; 435/456; 435/479; 435/69.1; 435/325; 935/11; 935/32; 800/18
[58] Field of Search ........................... 514/44; 435/320.1, 435/69.1, 235.1, 455, 456, 479, 325; 800/2, 18; 935/11, 32

[56] References Cited

FOREIGN PATENT DOCUMENTS

WO 90/06757 6/1990 WIPO .
WO 92/07945 5/1992 WIPO .
WO 93/03769 3/1993 WIPO .

OTHER PUBLICATIONS

Embase Database Abstracts 9200254, Frolkis et al. 1991.
WPI Database Abstracts 89–119, 1989.
Coghland, Focus, vol. 145, pp. 14–15, Nov. 25, 1995.
Brown, "News Media Researchers 'Oversold' Gene Therapy . . . Says", The Washington Post, Dec. 8, 1995.
Mulligan, Science, vol. 260, pp. 926–930, May 14, 1993.
Chan, Current Opinion in Lipidology, vol. 6, pp. 335–340, Oct. 1995.
Bramson et al., Current Opinion in Biotechnology, vol. 6, pp. 590–595, Oct. 1995.
Kashyap et al., Journal of Clinical Investigation, vol. 96, pp.1612–1620, Sep. 1995.
Rojanasakul, Advanced Drug Delivery Reviews, vol. 18, pp. 115–131, 1996.
Marshall, Science, vol. 269, pp. 1050–1055, Aug. 25, 1995.
Orkin & Motulsky, The Report and Recommendations of the Panel . . . Gene Therapy, Dec. 7, 1995.
Karathanasis et al., Proc. Natl. Acad. Sci., vol. 80, pp. 6147–6151, Oct. 1983.
Rosenfield et al., Cell, vol. 68, pp. 143–155, Dec. 10, 1992.

*Primary Examiner*—Jasemine C. Chambers
*Assistant Examiner*—Jill D. Schmuck

[57] ABSTRACT

The present invention concerns defective recombinant adenoviruses containing an inserted gene encoding apolipoproteins, pharmaceutical compositions comprising the adenovirus, and their use for the treatment or prevention of pathologies linked to dyslipoproteinemias.

11 Claims, 11 Drawing Sheets

RECOMBINANT ADERO VIRUSES COMPRISING AN INSERTED GENE ENCODING APOLIPOPROTEIN AND THEIR USE IN GENE THERAPY FOR DYSLIPOPROTEINEMIAS

BACKGROUND OF THE INVENTION

1. Field of the Invention

"This 371 application claims the benefit of PCT/FR94/00422, filed Nov. 10, 1994, which claims the benefit of French application FR93/05125, filed Apr. 30, 1993."

The present invention relates to new recombinant viruses, to their preparation and to their use in gene therapy, for the transfer and expression in vivo of desired genes. More specifically, it relates to new recombinant viruses comprising an inserted gene whose expression in vivo makes it possible to regulate the plasma levels of apolipoproteins. The present invention also relates to pharmaceutical compositions comprising the said recombinant viruses. More particularly, the present invention relates to defective recombinant viruses and to their use for the prevention or treatment of pathologies linked to dyslipoproteinemias which are known for their serious consequences at the cardiovascular and neurological level.

2. Description of Related Art

Dyslipoproteinemias are disorders of the metabolism of the lipoproteins responsible for the transport, in the blood and peripheral fluids, of lipids such as cholesterol and triglycerides. They result in major pathologies, linked respectively to hypercholesterolemia or hypertriglyceridemia, such as especially atherosclerosis. Atherosclerosis is a polygenic complex disease which is defined from the histological point of view by deposits (lipid or fibrolipid plaques) of lipids and of other blood derivatives in the wall of the large arteries (aorta, coronary arteries, carotid). These plaques, which are calcified to a greater or lesser extent according to the progression of their process, can be associated with lesions and are linked to the accumulation, in the arteries, of fatty deposits consisting essentially of cholesterol esters. These plaques are accompanied by a thickening of the arterial wall, with hypertrophy of the smooth muscle, the appearance of spumous cells and the accumulation of fibrous tissue. The atheromatous plaque is very clearly in relief on the wall, which confers on it a stenosing character responsible for vascular occlusions by atheroma, thrombosis or embolism which occur in the patients most affected. Hypercholosterolemias can therefore result in very serious cardiovascular pathologies such as infarct, sudden death, cardiac decompensation, cerebral vascular accidents and the like.

It is therefore particularly important to be able to have available treatments which make it possible to reduce, in certain pathological situations, the plasma cholesterol levels or even to stimulate the efflux of cholesterol (reverse transport of the cholesterol) in the peripheral tissues in order to discharge the cells having accumulated cholesterol within the context of the formation of an atheroma plaque. The cholesterol is carried in the blood by various lipoproteins including the low-density lipoproteins (LDL) and the high-density lipoproteins (HDL). The LDLs are synthesized in the liver and make it possible to supply the peripheral tissues with cholesterol. In contrast, the HDLs capture cholesterol in the peripheral tissues and transport it to the liver where it is stored and/or degraded.

At present, dyslipemias and in particular hypercholesterolemias are treated essentially by means of compounds which act either on the biosynthesis of cholesterol (inhibitors of hydroxymethylglutaryl-coenzymeA reductase, statins), or on the capture and elimination of bile cholesterol (sequestrants or resins), or alternatively on lipolysis by a mode of action which remains to be elucidated from the molecular point of view (fibrates). Consequently, all the major categories of drugs which have been used in this indication (sequestrants, fibrates or statins), are designed only for the preventive aspect of the formation of the atheroma plaque and not in fact for the treatment of the atheroma. The current treatment for atheroma, following a coronary accident, are only palliative since they do not act on cholesterol homeostasis and they are surgical acts (coronary by-pass, angioplasty).

The present invention constitutes a new therapeutic approach for the treatment of pathologies linked to dyslipoproteinemias. It proposes an advantageous solution to the disadvantages of the prior art, by demonstrating the possibility of treating pathologies linked to dyslipoproteinemias by gene therapy, by the transfer and expression in vivo of genes capable of regulating the plasma levels of apolipoproteins. The invention thus offers a simple means permitting a specific and effective treatment of these pathologies.

Gene therapy consists in correcting a deficiency or an abnormality (mutation, aberrant expression and the like) by introduction of a genetic information into the cell or affected organ. This genetic information can be introduced either in vitro into a cell extracted from the organ, the modified cell then being reintroduced into the body, or directly in vivo into the appropriate tissue. In this second case, various techniques exist, of which various techniques of transfection involving complexes of DNA and DEAE-dextran (Pagano et al., J. Virol. 1 (1967) 891), of DNA and nuclear proteins (Kaneda et al., Science 243 (1989) 375), of DNA and lipids (Felgner et al., PNAS 84 (1987) 7413), the use of liposomes (Fraley et al., J. Biol. Chem. 255 (1980) 10431), and the like. More recently, the use of viruses as vectors for the transfer of genes appeared as a promising alternative to these physical techniques of transfection. In this respect, various viruses were tested for their capacity to infect certain cellular populations, in particular the retroviruses (RSV, KMS, MKS, and the like), the HSV viruses, the adeno-associated viruses and the adenoviruses.

DETAILED DESCRIPTION OF THE INVENTION

The present invention constitutes a new therapeutic approach for the treatment of pathologies linked to dyslipoproteinemias, consisting in transferring and in expressing in vivo genes capable of regulating the plasma levels of apolipoproteins. The present invention also results from the demonstration that adenoviruses constitute particularly effective vectors for the transfer and expression of such genes. In particular, the present invention shows that the use of recombinant adenoviruses as vectors makes it possible to obtain sufficiently high levels of expression of these genes to produce the desired therapeutic effect. The present invention thus offers a new approach for the treatment and prevention of cardiovascular and neurological pathologies linked to dyslipoproteinemias.

A first subject of the invention therefore lies in a defective recombinant adenovirus containing at least one inserted gene whose expression makes it possible to regulate the levels of apolipoprotein in vivo.

The subject of the invention is also the use of such a defective recombinant adenovirus for the preparation of a pharmaceutical composition intended for the treatment or for the prevention of pathologies linked to dyslipoproteinemias.

The present invention is more particularly based on the demonstration that the adenovirus type viruses are capable of transferring and expressing genes encoding apolipoproteins in the liver, and of secreting the said apolipoproteins into the circulatory system where they exert their activity. The examples presented later indicate that adenoviruses are capable, according to the mode of administration, of effectively transferring and expressing, for a substantial period and without cytopathological effect, the genes encoding apolipoprotein AI or apolipoprotein AIV.

For the purposes of the present invention, the term "defective adenovirus" designates an adenovirus incapable of autonomously replicating in the target cell. Generally, the genome of the defective adenoviruses used within the framework of the present invention therefore lacks at least the sequences necessary for the replication of the said virus in the infected cell. These regions can be either removed (completely or partially), or rendered non-functional, or substituted by other sequences and especially by the inserted gene. Preferably, the defective virus conserves, nevertheless, the sequences of its genome which are necessary for the encapsulation of the viral particles.

There are various serotypes of adenoviruses, whose structure and properties vary somewhat. However, these viruses are not pathogenic for man, and especially for non-immunosuppressed subjects. Among these serotypes, the use of type 2 or 5 adenoviruses (Ad 2 or Ad 5) is preferred within the framework of the present invention. In the case of the Ad 5 adenoviruses, the sequences necessary for the replication are the E1A and E1B regions.

For the purposes of the present invention, the inserted gene capable of regulating the apolipoprotein levels in vivo may be a gene encoding an apolipoprotein or a protein product having an apolipoprotein type activity, or also an antisense gene, whose expression in the target cell makes it possible to control the expression of genes or the transcription of cellular mRNAs encoding apolipoproteins. The term protein product having an apolipoprotein type activity designates any mutant, fragment or peptide having at least one biological property of an apolipoprotein, as well as all natural variants of apolipoproteins.

The inserted gene may be a fragment of cDNA, of genomic DNA, or a hybrid construct consisting for example of a cDNA in which one or more introns would be inserted. It may also be synthetic or semisynthetic sequences.

Among the inserted genes for the purposes of the present invention, there may be mentioned more particularly the genes encoding all or an active part of the apolipoproteins AI, AIV or E.

The apolipoprotein AI is a protein consisting of 243 amino acids, which is synthesized in the form of a prepropeptide of 267 residues, having a molecular mass of 28,000 Daltons. It is synthesized in man specifically in the liver and the intestine and it constitutes the essential protein of the HDL particles (70% of their mass in proteins). It is abundant in plasma (1.0–1.2 g/l). Its best biochemically characterized activity is the activation of lecithin-cholesterol acyltransferase (LCAT), but numerous other activities are attributed to it, such as especially the stimulation of the efflux of cellular cholesterol. The physiological role of apolipoprotein AI appears to be counterbalanced by apolipoprotein AII since in man, the ratio of the two plasma concentrations (AII/AI) is very closely correlated with coronary risk. Apolipoprotein AI plays a major role in resistance to atherosclerosis, probably linked to the reverse transport of cholesterol, since the sole expression of this apolipoprotein in transgenic mice makes it possible to reduce 40-fold the surface area of the lipid deposits in the aorta compared with control mice (Rubin et al., 1993 Science, In Press). Its gene, 1863 bp in length, has been cloned and sequenced (Sharpe et al., Nucleic Acids Res. 12(9) (1984) 3917). Among the protein products with apolipoprotein AI type activity, there may be mentioned especially the natural variants described in the prior art (table below).

| Variant: | Mutation | Variant | Mutation |
| --- | --- | --- | --- |
| Milano | Arg173Cys | Norway | Glu136Lys |
| Marburg | Lys107∅ | | Pro165Arg |
| Munster2B | Ala158Glu | | Pro3His |
| Giessen | Pro143Arg | | Arg10Leu |
| Munster3A | Asp103Asn | | Gly26Arg |
| Munster3B | Pro4Arg | | Asp89Glu |
| Munster3C | Pro3Arg | | Lys107Met |
| Munster3D | Aup213Gly | | Glu139Gly |
| Munster4 | Glu198Lys | | Glu147Val |
| Yame | Asp13Tyr | | Ala158Glu |
| | Asp213Gly | | Glu169Gln |
| | | | Arg177His |

The apolipoprotein AIV (apoAIV) is a protein consisting of 376 amino acids, which is specifically synthesized in the intestine in the form of a precursor of 396 residue. The plasma protein is relatively abundant (0.16 g/l) and has a molecular mass of 46,000 Daltons. It is a major component of the chylomicrons secreted in the lymph, but it has the characteristic feature of being predominant in the form non-associated with lipoproteins in the plasma (R. B. Weinberg et al., 1983, J. Lipid. Research, 24: 52–59). Moreover, plasma apoAIV is polymorphic, although the nature of this polymorphism is still unknown (G. Utermann et al., 1982, J. Biol. Chem. 257: 501–507). The physiological role of apoAIV also remains somewhat unknown. It is known that it can activate, in vitro, lecithin-cholesterol acyltransferase (LCAT) (Steinmetz et al., 1985, J. Biol. Chem., 260: 2258–2264) and that it can, like apolipoprotein AI, interfere with the binding of the HDL particles onto bovine aortic endothelial cells (Savion et al., 1987, Eur. J. Biochem., 257: 4171–4178). These two activities indicate that apoAIV very probably acts as mediator of the reverse transport of cholesterol. The apoAIV gene has been cloned and described in the prior art (see especially WO 92/05253). Among the protein products with apolipoprotein AIV type activity, there may be mentioned especially the fragments and derivatives described in Patent Application FR 92 00806.

Apolipoprotein E comprises 317 residues of which 18 correspond to the signal peptide. There is no propeptide. The apoE gene has been cloned and sequenced (about 3600 bp) and encodes an mRNA of 1163 bp. apoE is distributed in the plasma between the VLDL and HDL particles. It represents about 10–20% of the VLDL proteins and 2% of the HDL proteins. The HDL-Es constitute a distinct subclass of HDLs. The plasma concentration of apoE is about 0.05 g/l. apoE is synthesized in the form of a sialo-protein which is then desialilated in the plasma. The synthesis of apoE is carried out by the liver and weakly by the intestine. However, contrary to the other apolipoproteins, apoE is also synthesized in numerous other tissues (brain, kidney, adrenal glands, reticuloendothelial cells and the like). apoE recognizes, with a very strong affinity, the LDL receptor (apoB/E receptor) but also another receptor on heptic cells not recognizing apoB (chylomicron/remnant receptor).

A polymorphism was demonstrated on the basis of different electrophoretic mobilities. Six major phenotypes (E2/2, E2/3, E2/4, E3/4, E3/3, E4/4) have thus been described. According to the studies carried out on large caucasian populations, the prevalence of the corresponding alleles would be 14–15% for ϵ4, 74–78% for ϵ3 and 8–12% for ϵ2. A difference exists among the Finnish for whom ϵ4 is more abundant (23%) and ϵ2 is less abundant (4%). The normal allele is ϵ3. The ϵ2 allele would correspond to the type III dyslipoproteinemia (E2/2 phenotype), a disease which is associated with an increase in cholesterol and triglycerides, xanthomas and with an early atherosclerosis. An association between the ϵ4 allele and familial Alzheimer's disease has been recently reported (Strittmatter et al., P.N.A.S. 99 (1993) 1977). More recently, the destruction of the apoE gene in mice has shown the appearance of a hypersusceptibility to atherosclerosis (E. Rubin et al. Cell 1992).

For the purposes for the invention, the term "inserted gene" also designates antisense sequences whose expression in the target cell makes it possible to control the expression of genes or the transcription of cellular mRNAs encoding apolipoproteins. Such sequences can for example be transcribed, in the target cell, into RNA complementary to cellular mRNAs and thus block their translation into protein.

Among the antisense sequences which can be used within the framework of the invention, there may be mentioned more particularly any antisense sequence which makes it possible to reduce the levels of production of apolipoprotein AII, as illustrated in the examples.

Generally, the inserted gene also comprises sequences permitting its expression in the infected cell. These may be sequences which are naturally responsible for the expression of the said gene when these sequences are capable of functioning in the infected cell. They may also be sequences of different origin (which are responsible for the expression of other proteins, or even synthetic). In particular, they may be sequences of eukaryotic or viral genes. As example, they may be promoter sequences derived from the genome of the cell which it is desired to infect, or from the genome of a virus, and especially the promoters of the adenovirus genes E1A and MLP, the promoter CMV, LTR-RSV, and the like. In addition, these expression sequences can be modified by addition of activating and regulatory sequences and the like. Moreover, when the inserted gene does not contain expression sequences, it can be inserted into the genome of the defective virus downstream of such a sequence.

Moreover, when the inserted gene encodes an apolipoprotein or a protein product with apolipoprotein type activity, it generally comprises, upstream of the coding sequence, a signal sequence directing the synthesized polypeptide in the secretion pathways of the target cell. This signal sequence may be the natural signal sequence of the apolipoprotein, but it may also be any other functional signal sequence or an artificial signal sequence.

The defective recombinant adenoviruses according to the invention can be prepared by homologous recombination between an adenovirus and a plasmid carrying, inter alia, the gene which it is desired to insert. The homologous recombination occurs after cotransfection of the said adenovirus and plasmid into an appropriate cell line. The cell line used should preferably (i) be transformable by the said elements, and (ii) contain the sequences capable of complementing the defective adenovirus genome part, preferably in integrated form in order to avoid the risks of recombination. As an example of a line, there may be mentioned the human embryonic kidney line 293 (Graham et al., J. Gen. Virol. 36 (1977) 59) which contains especially, integrated in its genome, the left-hand part of the genome of an Ad5 adenovirus (12%).

Then, the vectors which have multiplied are recovered and purified according to conventional molecular biology techniques.

The present invention also relates to a pharmaceutical composition containing one or more defective recombinant adenoviruses as described above. Such compositions can be formulated for topical, oral, parenteral, intranasal, intravenous, intramuscular, subcutaneous or intraocular administration and the like.

Preferably, the composition contains vehicles pharmaceutically acceptable for an injectable formulation.

In their use for the treatment of pathologies linked to dyslipoproteinemias, the defective recombinant adenoviruses according to the invention can be administered according to various modes, especially by intravenous injection. Preferably, they are injected at the level of the portal vein.

The doses of virus used for the injection can be adapted according to various parameters, especially according to the mode of administration used, the pathology concerned, the gone to be expressed, or alternatively the duration of treatment desired. Generally, the recombinant adenoviruses according to the invention are formulated and administered in the form of doses of between $10^4$ and $10^{14}$ pfu/ml and, preferably $10^6$ to $10^{10}$ pfu/ml. The term pfu ("plaque forming unit") corresponds to the infectivity of a suspension of virions, and is determined by infection of an appropriate cell culture, and measurement, generally after 48 hours, of the number of plaques of infected cells. The techniques for determining the pfu titre of a viral solution are well documented in the literature.

The present invention thus offers a very effective means for the treatment or prevention of pathologies linked to dyslipoproteinemias, in particular in the domain of cardiovascular conditions such as myocardial infarction, angina, sudden death, cardiac decompensation, cerebrovascular accidents, or in the domain of neurological conditions where certain apolipoproteins such as apoE appear to play an important role (diseases of neuronal aging, familial Alzheimer, neuronal regeneration). More generally, this approach offers a very promising therapeutic procedure for each case where a deficiency of a genetic or metabolic nature of a plasma apolipoprotein can be corrected.

In addition, this treatment can be applied both to man and to any animal such as ovines, bovines, domestic animals (dogs, cats and the like), horses, fish, and the like.

The present invention is more completely described with the aid of the following examples which should be considered as illustrative and non-limiting.

GENERAL MOLECULAR BIOLOGY TECHNQUES

Figure 1:
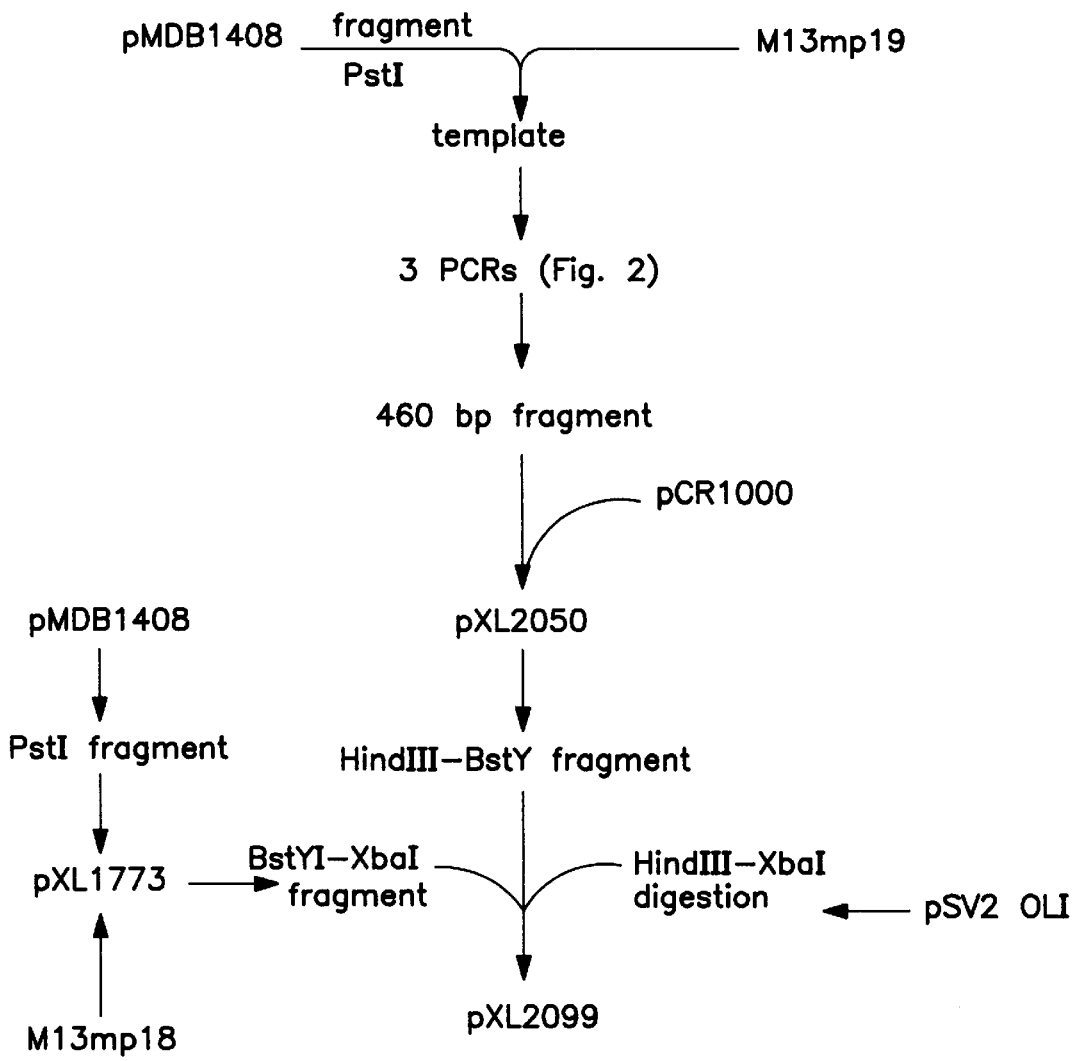
FIG. 1: Strategy for the construction of the plasmid pXL2099.
Figure 2:
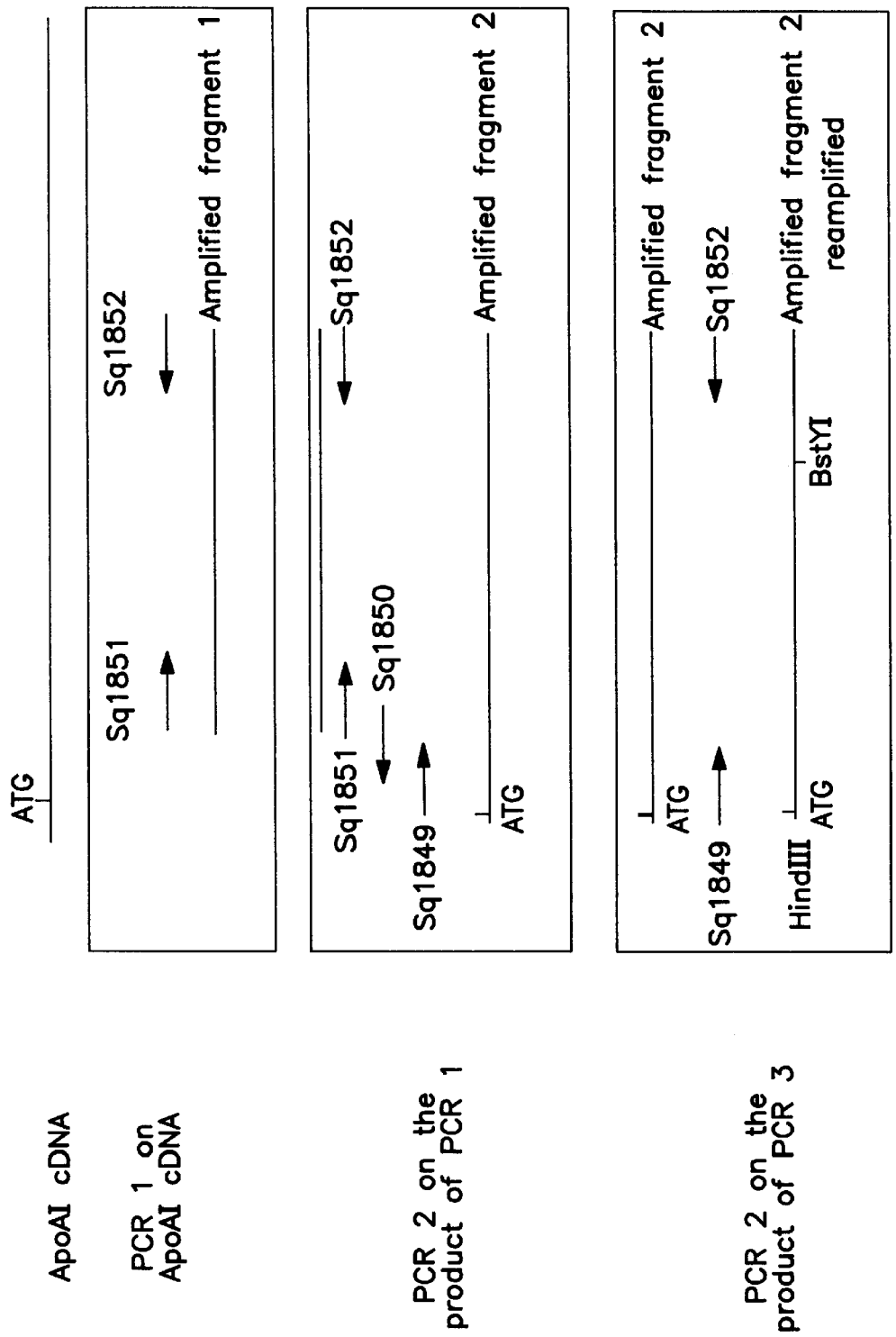
FIG. 2: Strategy for amplification of the apoAI cDNA.

The methods conventionally used in molecular biology, such as preparative extractions of plasmid DNA, centrifugation of plasmid DNA in caesium chloride gradient, agarose or acrylamide gel electrophoresis, purification of DNA fragments by electroelution, phenol or phenol-chloroform extraction of proteins, ethanol or isopropanol precipitation of DNA in saline medium, transformation in *Escherichia coli* and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, Now York, 1987].

The pBR322 and pUC type plasmids and the phages of the M13 series are of commercial origin (Bethesda Research Laboratories).

For the ligations, the DNA fragments can be separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier.

The filling of the protruding 5' ends can be performed with the Klenow fragment of *E. coli* DNA polymerase I (Biolabs) according to the specifications of the supplier. The destruction of the protruding 3' ends is performed in the presence of phage T4 DNA polymerase (Biolabs) used according to the recommendations of the manufacturer. The destruction of the protruding 5' ends is performed by a controlled treatment with S1 nuclease.

Site-directed mutagenesis in vitro by synthetic oligodeoxynucleotides can be performed according to the method developed by Taylor et al. [Nucleic Acids Res. 13 (1985) 8749–8764] using the kit distributed by Amersham.

The enzymatic amplification of the DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] can be performed using a DNA thermal cycler (Perkin Elmer Cetus) according to the specifications of the manufacturer.

The verification of the nucleotide sequences can be performed by the method developed by Sanger et al. [Proc. Natl. Acad. Sci. USA, 74 (1977) 5463–5467] using the kit distributed by Amersham.

EXAMPLES

Example A

Construction of a defective recombinant adenovirus containing the apolipoprotein AI gene As indicated above, the defective recombinant adenoviruses were prepared by homologous recombination between an adenovirus and a plasmid carrying, inter alia, the gene which it is desired to insert, after cotransfection into an appropriate cell line.

A1 preparation of the plasmids carrying the apoAI gene (see FIGS. 1–4)

The plasmids used to generate, by homologous recombination, the recombinant adenoviruses expressing the human apolipoprotein AI gene were constructed as follows:

1. Construction of the plasmid pXL2236

The plasmid pXL2236 contains especially the cDNA encoding the preproApoAI under the control of the CMV promoter, the polyadenylation signals of the SV40 virus, as well as an adenovirus region permitting the homologous recombination.

Figure 3:
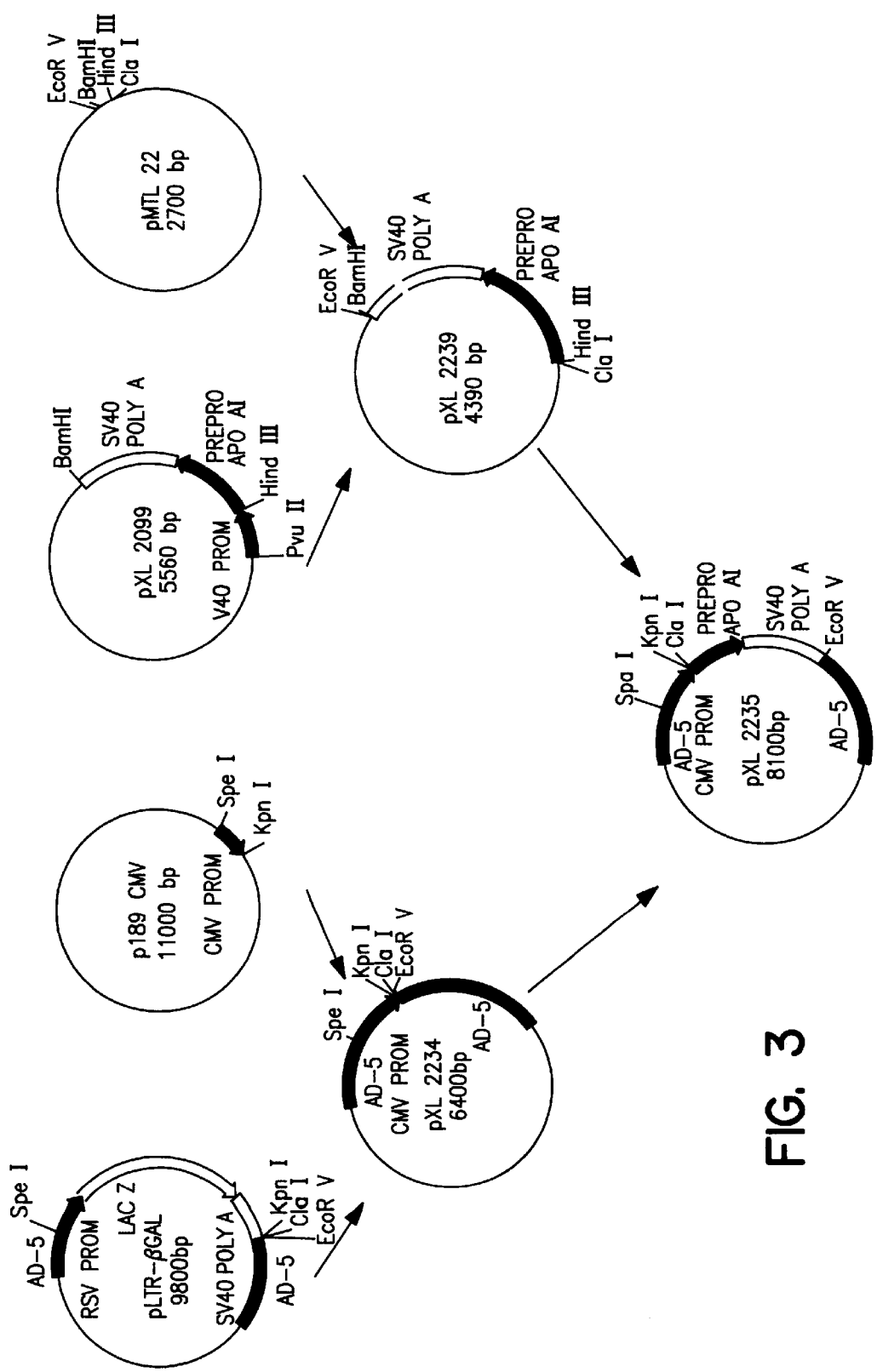
FIG. 3: Construction of the plasmid pXL2235.

It was constructed in the following manner:

The DNA fragment corresponding to the human apoAI cDNA was isolated in the form of PstI fragment from the vector pMD1408 described by S. Law and B. Brewer Jr. (PNAS 81 (1984) 66–70). This fragment was introduced into the plasmid M13mp19 (FIG. 1). This fragment was then modified by successive PCRs (FIG. 2) in order to introduce a HindIII site in the 5' position. Thus, a first PCR reaction was carried out on the plasmid obtained above by means of the oligonucleotides Sq1851 (SEQ ID No. 1) and Sq1852 (SEQ ID No. 2). The DNA derived from this PCR was reamplified in a second PCR with the oligonucleotides Sq1849 (SEQ ID No. 3), Sq1850 (SEQ ID No. 4), Sq1851 and Sq1852. A third PCR was finally carried out using the result of the second PCR with the oligonucleotides Sq1849 and Sq1852. The fragment of about 460 bp obtained was cloned into the plasmid PCR1000 (Invitrogen) and its sequence verified. The resulting plasmid was called plasmid pXL2050 (FIG. 1). The fragments HindIII-BstY1 from pXL2050 and BstY1-XbaI from pXL1773 (PstI fragment from the plasmid pMDB1408 inserted into M13mp18) were then cloned into the plasmid pSV2 OLI (Subramani et al., MCB 1 (1991) 854) previously digested with HindIII-XbaI, to generate the plasmid pXL2099 (FIG. 3).

The SpeI-XpnI fragment carrying the cytomegalovirus (CMV) promoter was then isolated from the vector pEB-VDdyadCMVlacIn (p189 CMV, Biard et al., Biochemichal and Biophysical Acta 1130 (1992) 68), and then inserted into the corresponding sites of the vector pRSV-βgal (Stratford-Perricaudet et al., J. Clin. Invest. 90 (1992) 626). The plasmid obtained was designated pXL2234. During this step, the coding regions RSV LTR and lac Z are removed. Then the HindIII-BamHI fragment at the blunt ends, containing the region encoding preproApoI as well as the signals for maturation of the SV40 virus mRNA, was isolated from the plasmid pXL2099 and then inserted at the EcoRV site of the plasmid pXL2234.

The plasmid thus obtained was designated pXL2236.

2. Construction of the plasmid pXL2235

A second plasmid, designated pXL2235, was constructed. This plasmid contains espcially the cDNA encoding preproApoAI under the control of the CMV promoter, the polyadenylation signals of the SV40 virus, as well as an adenovirus region permitting the homologous recombination.

It was obtained in two steps:
  insertion of the HindIII-BamHI fragment from the plasmid pXL2099 identified above, into the vector pMTL22 (Chambers et al., Gene 68 (1988) 139) digested with the same enzymes, and then,
  digestion of the plasmid obtained above with the enzymes ClaI-EcoRV and insertion of the ClaI-EcoRV fragment thus isolated into the plasmid pXL2234 digested with EcoRV.

The plasmid thus obtained was designated pXL2235 (FIG. 3).

3. Construction of the plasmid pXL2244

The plasmid pXL2244 contains the ApoAI cDNA under the control of the RSV virus LTR promoter. It was constructed by insertion of the ClaI-EcoRV fragment from pXL2239 into the vector pLTR RSV-βgal digested with the same enzymes.

Figure 4A:
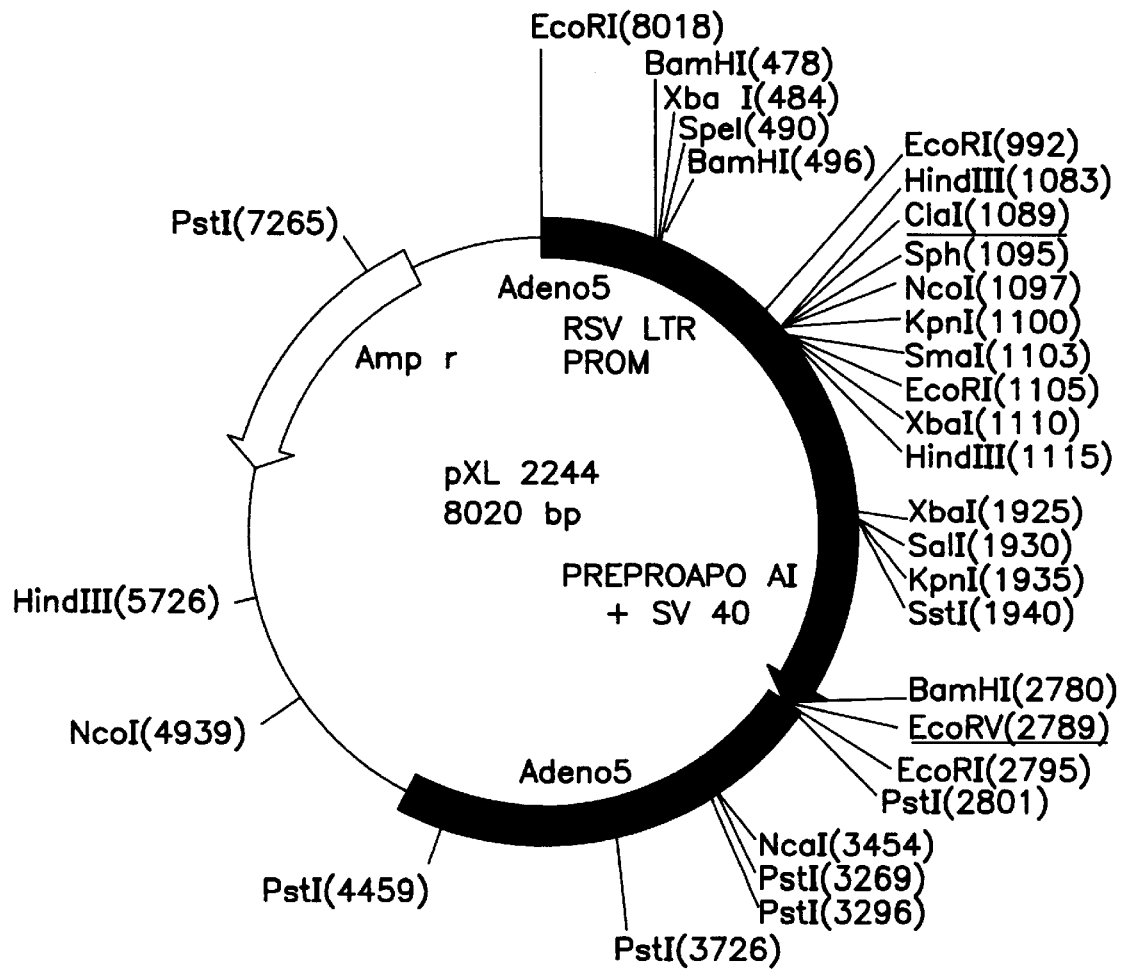
FIG. 4A and 4B: Representation of the plasmids pXL2244 and pXL2263.
Figure 4B:
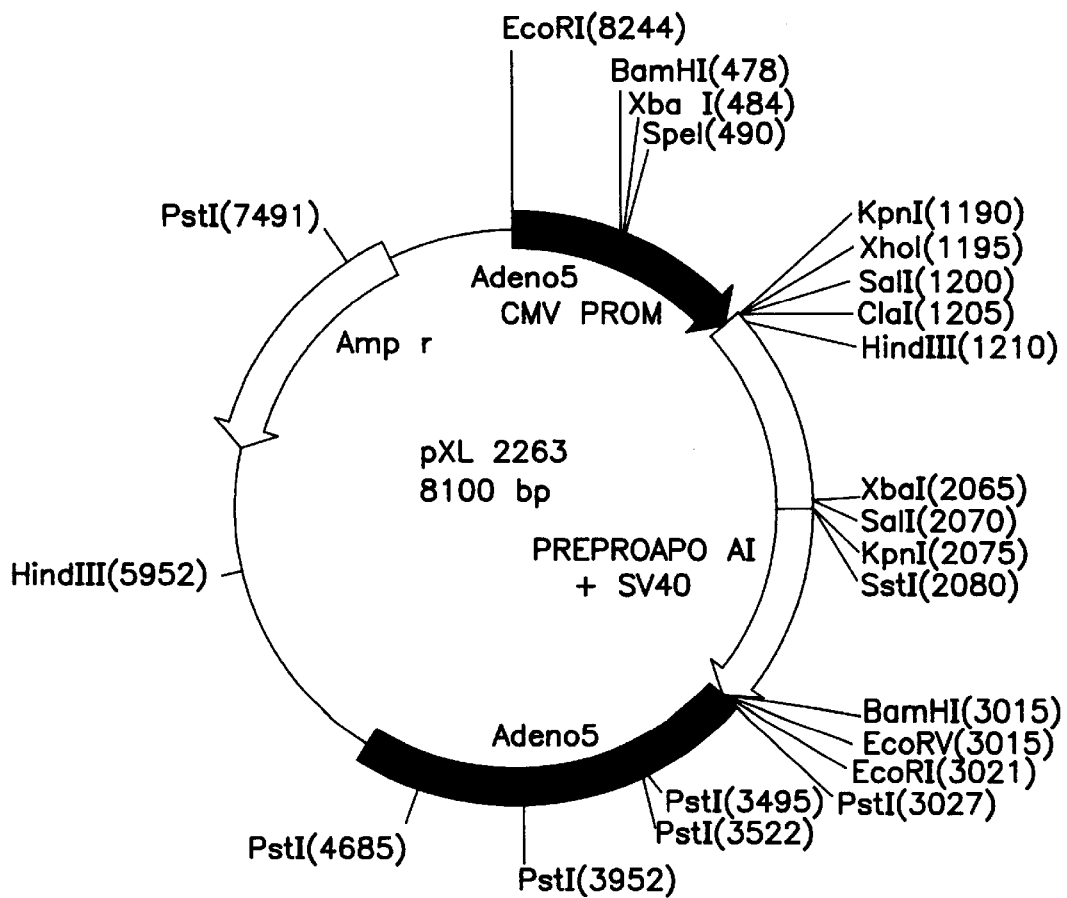

The structure of the plasmid pXL2244 is given in FIG. 4.

4. Construction of the plasmid pXL2263

The plasmid pXL2263 is derived from the vector pXL2235 from which a portion of the polylinker separating the CKV promoter from the ApoAI cDNA (KpnI fragment) has been deleted. It was constructed in two steps:

First, the HindIII-BamHI fragment from pXL2099, containing the ApoAI cDNA and the SV40 fragment, was cloned into the same sites of a plasmid pBluescript, to give rise to the plasmid pXL2245.

Then the KpnI fragment containing the ApoAI cDNA of this plasmid was recloned in the correct orientation into the vector pXL2235 digested with KpnI.

The structure of the plasmid pXL2263 is given in FIG. 4.

5. Construction of the plasmid pXL2336

The plasmid pXL2336 contains a hybrid construct between a genomic sequence containing the promoter, the first axon and the first intron of the apoAI gene and the sequence of the apoAI cDNA sequence.

Figure 5:
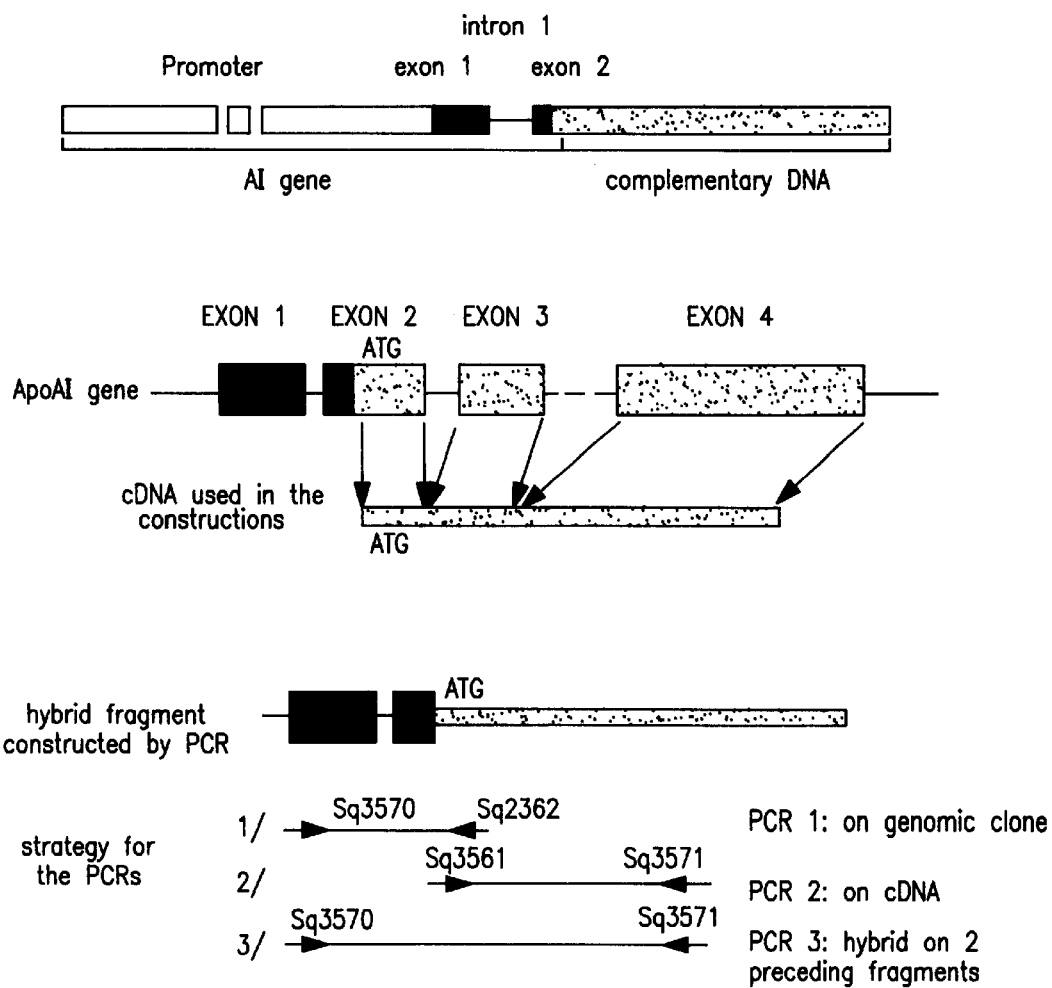
FIG. 5: Strategy for the construction of the ApoAI minigene.

For that, the hybrid sequence described in FIG. 5 was constructed by PCR as described below.

The primers used are Sq3561 (SEQ ID No. 5) and Sq3571 (SEQ ID No. 6) which amplify the sequence from base 14 to base 441 of the ApoAI cDNA as well as Sq3570 (SEQ ID No. 7) and Sq3562 (complementary to Sq3561) which amplify a fragment stretching from the promoter, including a unique AflII site, to the beginning of the second exon. Both fragments, which are therefore complementary to the primers Sq3561 and Sq3562, were then purified on a gel, mixed and used as template for a second PCR with the primers Sq3571 and Sq3570. The hybrid fragment is then cloned into pCRII (Invitrogen), resulting in the plasmid pXL2314, and its sequence verified.

A fragment from XL2314, cut with XhoI, filled with Klenow and then recut with AflII, was then cloned into the plasmid pXL2068, previously digested with HindIII, filled with Klenow and recut with AflII. The plasmid pXL2068 contains the ApoAI promoter from the KpnI site situated towards the base −2200 up to the KpnI site situated after the site of initiation of transcription (base+93), cloned into a plasmid pUC19 with the 5' end of the promoter of the dimensioned of the EcoRI site, then recloned by the sites XbaI and SstI into the plasmid pSL301 (Invitrogen). The resulting plasmid is called pXL2318.

Figure 6:
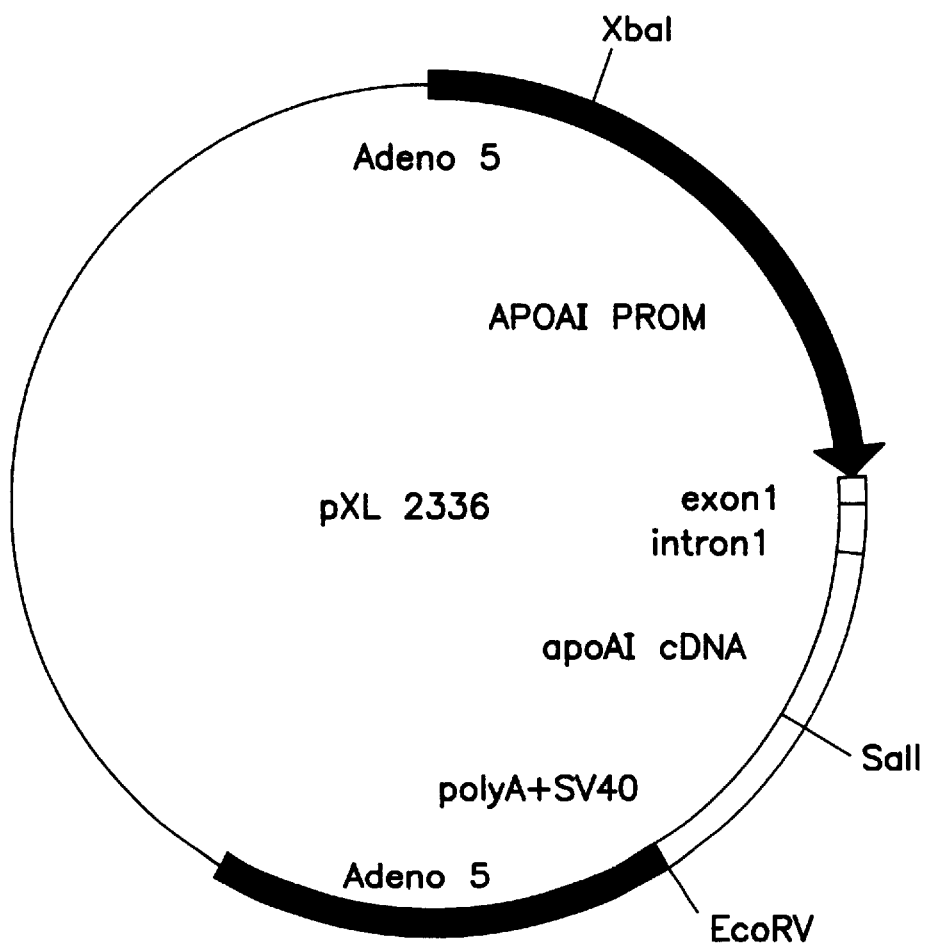
FIG. 6: Representation of the plasmid pXL2336.

A XbaI-Bsu36I fragment from pXL2318 is finally cloned into the plasmid pXL2263 described above and partially cut with SpeI and then Bsu36I. The resulting plasmid is finally called pXL2336 and its structure is given in FIG. 6.

6. Construction of the plasmid PXL2375

This plasmid contains the ApoAI cDNA under the control of the CMV promoter stretching up to the splice-giving 5' site linked to the 3'-most 107 base pairs of the synthetic intron described by O'Gorman et al (Science, 1991, 251:1351–1355) which then provide the 3' site for splicing.

Figure 7:
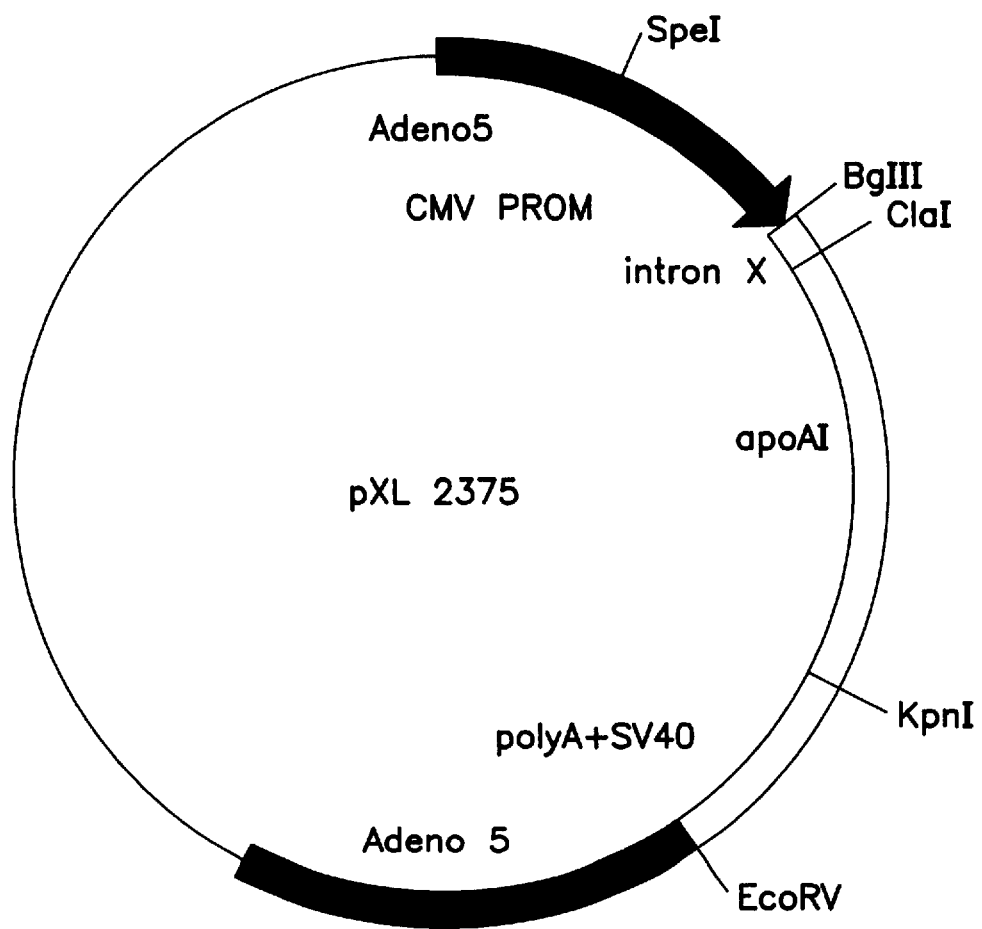
FIG. 7: Representation of the plasmid pXL2375.

This promoter is removed from the plasmid pAICMVIX-CAT.3 (Philip et al., Molecular and Cellular Biology, in press) by the XbaI and ClaI sites and cloned at the same sites in the vector pXL2263 to give plasmid pXL2375. Its map is given in FIG. 7.

A2. Expression of apoAI in vitro

The vectors described in A1 were tested for their functionality, by expression in the lines Cos1 or Cos7. For that, the vectors were introduced into the cells by electroporation, according to the procedure described by P. Benoit et al., Journal of Immunology 150 (1993) 707.

48 hours after the transfection, the cellular supernatants were recovered and tested for their ApoAI content by an ELISA test. For that, Immulon II plates (Dynatech) were coated with an anti-ApoAI monoclonal antibody (10 mg/ml in carbonate buffer, pH 9.6), by overnight incubation at 4° C., then saturated with 2% BSA in PBS, pH 7.4, for one hour at 37° C. The cellular supernatants were then incubated for one hour at 37° C., optionally after dilution with PBS 2% BSA. The revealing was then carried out by incubation for one hour at 37° C. with a mixture of peroxidase-labelled anti-ApoAI monoclonal antibodies, and diluted 1/5000. The binding of the peroxidized antibodies is finally revealed by incubation with 250 $\mu$l of TMB (KPL) and reading the plates at 630 nm.

The results obtained shows that, in all the tested cases, the expression of ApoAI can be detected.

A3. Preparation of the recombinant adenoviruses

The plasmids prepared in A1 were then linearized and cotransfected for recombination with the deficient adenoviral vector, into the helper cells (line 293) supplying in trans the functions encoded by the adenovirus E1 regions (E1A and E11B).

The adenovirus Ad.CMVApoAI was obtained by homologous recombination in vivo between the adenovirus Ad.RSVβgal (Stratford-Perricaudet et al., J. Clin. Invest 90 (1992) 626) and the plasmid pXL2235, according to the following procedure: subsequently, the plasmid pXL2235, linearized with the enzyme EagI and the adenovirus Ad.RSVβgal, linearized with ClaI, are cotransfected into the line 293 in the presence of calcium phosphate, to allow homologous recombination. The recombinant adenoviruses thus generated are selected by purification on plates. After isolation, the recombinant adenovirus is amplified in the 293 cell line, giving a culture supernatant containing the unpurified recombinant defective adenovirus having a titre of about $10^{10}$ pfu/ml.

The viral particles are generally purified by caesium chloride gradient centrifugation according to known techniques (see especially Graham et al., Virology 52 (1973) 456). The adenovirus Ad.CMVApoAI is preserved at −80° C. in 20% glycerol.

The same procedure was reproduced with the plasmid pXL2244, resulting in the recombinant adenovirus Ad.RSVApoAI.

Example B
Transfer and expression in vivo of the apoAI gene

The stock of virus which is thus produced is then used for the infection in vivo.

In the first instance, the viruses are used for the in vivo infection of hepatocytes in mice. For that, the viral particles are injected, for example via the portal route, in C57B16 mice. The mode of injection and the specificity of expression were tested by a prior study performed with viruses expressing β-galactosidase (an injection technique which can be used has also been described by Jaffe et al., Nature Genetics, vol. 1 (1992) 372). The level of plasma expression of human apoAI is tested by ELISA with the aid of monoclonal antibodies specific for the human protein, and the specificity of the expression of the recombinant gene is verified with the aid of specific human oligonucleotide probes in different tissues (Northern blotting and RT-PCR).

These viruses, called Ad(RSV-ApoAI) and Ad(CMV-ApoAI), are intravenously injected into C57B1/6 mice using the caudal vein or the retro-orbital sinus. They are injected into ApoAI knock-out mice (Williamson et al., 1992, Proc. Natl. Acad. Sci. USA, 89:7134–7138), in which the mouse ApoAI is not expressed and in which HDL cholesterol is very low, which makes it possible to have a very clean background so as to see the effects of the expression of human ApoAI. This expression is tested by an ELISA, with the aid of monoclonal antibodies specific for the human protein, modified according to Betard et al. (J. Clin. Chem. Clin. Biochem., 1987, 25:893–899).

B1. Expression in ApoAI Knock-out mice

Figure 8:
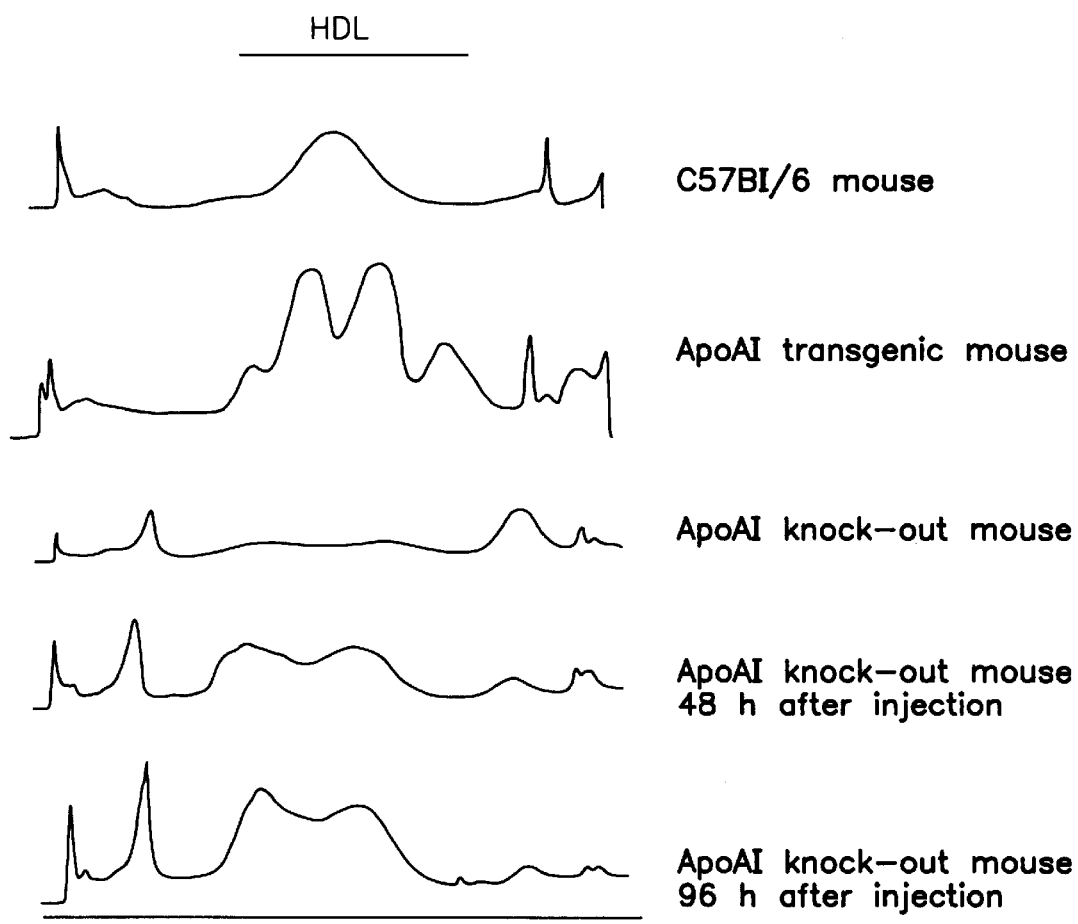
FIG. 8: Effect of the injection of an adenovirus ApoAI on the HDL profile.

The virus Ad(CMV-ApoAI) is first injected into ApoAI Knock-out mice which are therefore deficient in the expression of mouse ApoAI. After injection of $10^9$ pfu via the caudal vein, the human apoAI is found at the concentration of 0.3 mg/dl in the plasma after 48 h and 96 h. The HDL-cholesterol concentration is also measured at the same time, which makes it possible to measure an increase of 8 mg/dl before the injection at levels of 30–35 mg/dl at 48 and 96 hours. These mice, injected with Ad(CMV-ApoAI) make it possible to demonstrate a lipoprotein profile corresponding to human type HDLs with a polydisperse HDL population which is also found in tranagenic mice for the human ApoAI gene in which the major component of the HDLs has become human ApoAI. By comparison, in a normal mouse, the HDL profile corresponds in size to a single population of particle and in the ApoAI Knock-out mice, the profile is flat in the corresponding region and a HDL population of abnormal size exists (FIG. 8).

B2. Expression in C57B1/6 mice

Figure 9A:
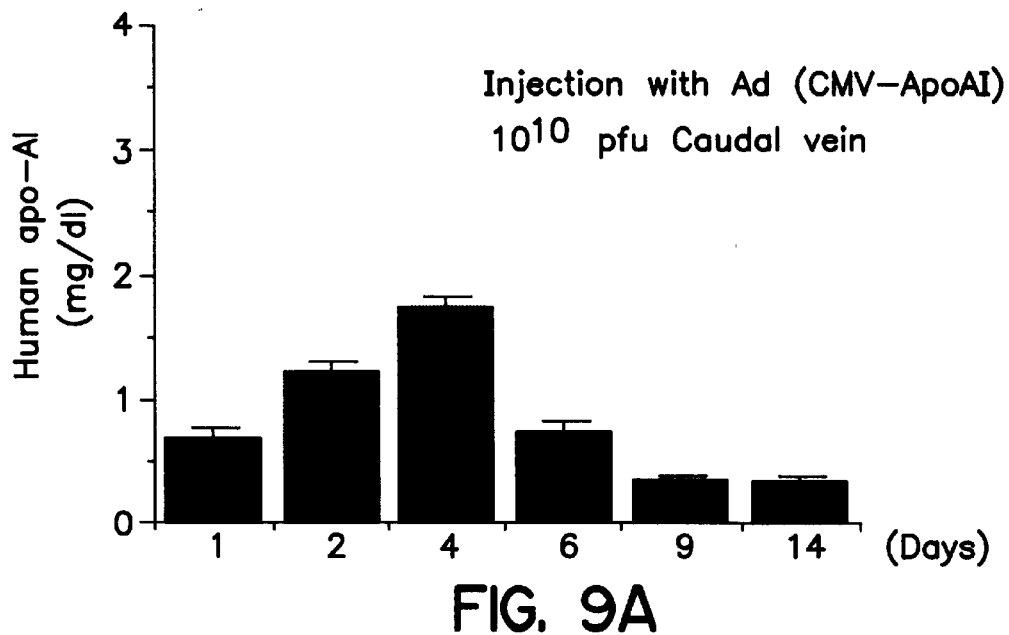
FIG. 9A and B: Effect of the injection of an ApoAI adenovirus on the plasma levels of ApoAI.
Figure 9B:
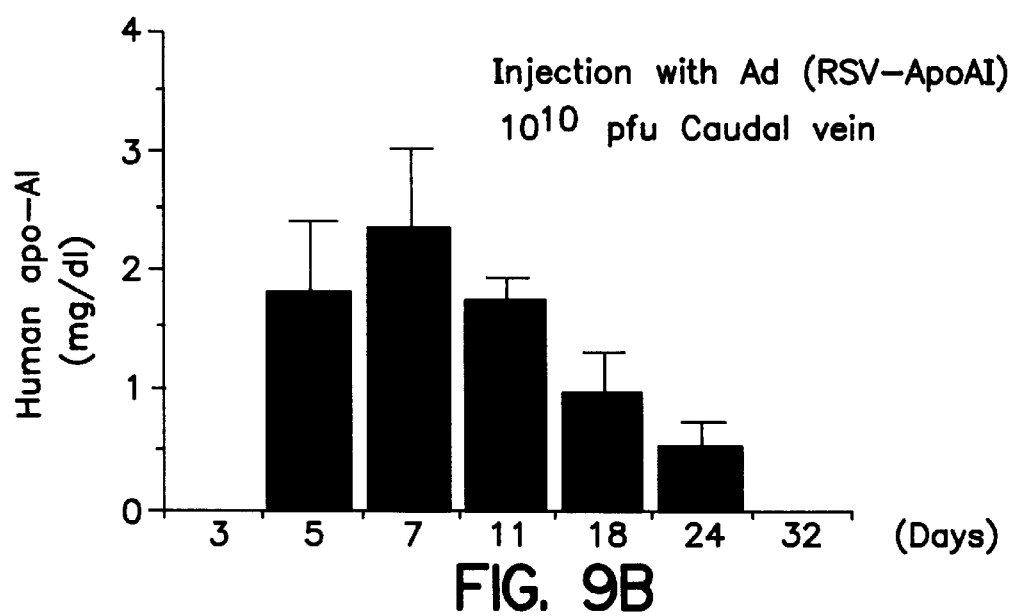

Human ApoAI levels of the order of 1 to 5 mg/dl are found in the plasma of mice injected with $10^{10}$ pfu of the viruses Ad(RSV-ApoAI) or Ad(CMV-ApoAI). Equivalent levels are found after an injection via the caudal vein or via the retro-orbital sinus. This expression is stable for about 15 days in the case of the CMV promoter by lasts for the order of 4 weeks in the case of the RSV promoter (FIG. 9).

Example C

Construction of a defective recombinant adenovirus containing an apolipoprotein AII antisense gene C1. Preparation of the plasmids carrying an apoAII antisense gene 1. Construction of the plasmid pXL2264

The plasmid pXL2264 contains the cDNA encoding human apolipoprotein A-II.

It was constructed in the following manner:

The DNA fragment corresponding to the apoA-II cDNA was isolated by the RT-PCR technique from total RNAs from HepG2 cells. The cDNAs were produced by reverse transcription of the polyA+ RNAs using oligodT primers. One PCR was then carried out on these cDNAs with the oligonucleotides Sq3319 and Sq3320 (SEQ ID No. 8 and 9), which are specific for the apoA-II sequence (Chan et al., Meth. Enzymol. 128 (1986) 745). The 473 bp fragment obtained was cloned into the plasmid pCRII (Invitrogen) and its sequence verified. The 5' part of the coding strand of the cDNA is beside the HindIII site of pCRII and the 3' part beside the XhoI site. The resulting plasmid was called pXL2264.

2. Construction of plasmid pXL2267

The plasmid pXL2267 contains the cDNA encoding the complete human apolipoprotein A-II antisense gene (SEQ ID No. 12).

It is one of the clones obtained by cloning the 473 bp PCR fragment into the plasmid pCR-II (cf. 1 above). Its sequence was verified. The A-II cDNA is in the opposite orientation compared with the cDNA carried by the plasmid pXL2264 (5' part of the coding strand beside the XhoI site and 3' part close to the HindIII site).

3. Construction of the plasmid 1pXL2268

The plasmid pXL2268 contains the cDNA encoding a human apolipoprotein A-II partial antisense gene whose sequence is complementary to that of the A-II cDNA for the bases +1 to +95 and +307 to +473 (SEQ ID No. 13).

It was constructed in the following manner:

Two PCRs were carried out on the plasmid pXL2264 (carrying the sense A-II), one with the oligonucleotides Sq3319 and Sq3369, the other with the oligonucleotides Sq3320 and Sq3364 (SEQ ID No. 10). The fragments derived from these PCRs are 96 and 167 bp respectively. A third PCR was performed on a mixture of these two fragments with the oligonucleotides Sq3319 and Sq3320. The 263 bp fragment obtained was cloned into the plasmid pCRII (Invitrogen) and its sequence verified. The 5' part of the coding strand of the A-II cDNA is beside the XhoI site of pCRII. The resulting plasmid was called pXL2268.

4. Construction of the plasmid pXL2269

The plasmid pXL2269 is a eukaryotic expression vector containing the cDNA of the human apolipoprotein A-II gone under the control of the RSV virus LTR sequence.

It was constructed in the following manner:

digestion of the plasmid pXL2264 with HindIII-XhoI, and then, insertion of the HindIII-XhoI fragment containing the apoA-II sense cDNA into the vector pREP4 (Invitrogen) previously digested with the same enzymes.

5. Construction of the plasmids pXL2270 and pXL2271

The plasmids pXL2270 and pXL2271 are eukaryotic expression vectors containing the cDNAs of the human apolipoprotein A-II complete and partial antisense genes respectively, under the control of the CMV virus promoter regions.

They were constructed in the following manner:

digestion of the plasmids pXL2267 and pXL2268 with HindIII-XhoI, and then, insertion of the HindIII-XhoI fragments from each plasmid, containing the apoA-II antisense cDNAs, into the vector pCEP4 (Invitrogen) previously digested with the same enzymes.

The plasmids thus obtained were designated pXL2270 (complete antisense) and pXL2271 (partial antisense) respectively.

6. Construction of the plasmid pXL2403

The plasmid pXL2403 is a euaryotic expression vector containing especially the cDNA encoding the human apolipoprotein A-II under thecontrol of the adenovirus MLP promoter, the polyadenylation signal sequence and the SV40 virus replication origin.

It was constructed in the following manner:

digestion of the plasmid pXL2264 with EcoRI, and then, insertion of the EcoRI—EcoRI fragment containing the apoA-II sense cDNA into the vector pMT3 (Swick et al., PNAS 89 (1992) 1812), previously linearized with EcoRI. The plasmid, selected for the correct orientation of the sense cDNA, was designated pXL2403.

7. Construction of the plasmid pXL2404

The plasmid pXL2404 is a eukaryotic expression vector containing a cDNA encoding a messenger RNA whose sequence is complementary to the entire sequence of the mRNA encoding the humanapolipoprotein A-II. It was constructed according to the same technique as the plasmid pXL2403 but it was selected for the opposite orientation of the sense cDNA. The plasmid thus obtained was called pXL2404.

8. Construction of the plasmid pXL2405

The plasmid pXL2405 contains the cDNA encoding VA $RNA_I$, RNA from the type 2 adenovirus whose transcription is in dependence on RNA polymerase III.

It was constructed in the following manner:

The DNA fragment corresponding to VA RNA$_f$ was isolated by the PCR technique from the genomic DNA from the type 2 adenovirus by means of the oligonucleotides VACla5' (SEQ ID No. 14) and VACla3' (SEQ ID No. 15). The 238 bp fragment obtained was purified and cloned into the plasmid pCR-II (Invitrogen). The plasmid thus obtained was called pXL2405.

9. Construction of the plasmid pXL2406

The plasmid pXL2406 contains the cDNA encoding VA RNA$_f$, whose sequence is modified by insertion, at position 102, of a 33 nucleotide sequence complementary to the sequence +44 /+76 of the cDNA encoding human apoA-II (SEQ ID No. 21).

It was constructed in the following manner:

Two PCRs were carried out on the type 2 adenovirus genomic DNA, one with the oligonucleotides Sq3892 (SEQ ID No. 16) and VACla5', and the other with the oligonucleotides VACla3' and Sq3893 (SEQ ID No. 17). The fragments derived from these PCRs are 162 and 118 bp respectively. A third PCR was performed on a mixture of these two fragments, after their purification by means of the oligonucleotides VACla5' and VACla3'. The 271 bp fragment obtained was cloned into the plasmid pCRII (Invitrogen) and its sequence verified over 254 bp (SEQ ID No. 22). The resulting plasmid was called pXL2406.

10. Construction of the plasmid pXL2407

The plasmid pXL2407 contains the cDNA encoding VA RNA$_f$, whose sequence is modified by insertion, at position 102, of a 33 nucleotide sequence complementary to the sequence +441/+473 of the cDNA encoding human apoA-II (SEQ ID No. 23).

It was constructed in the following manner:

Two PCRs were carried out on the type 2 adenovirus genomic DNA, one with the oligonucleotides VACla5' and Sq3894 (SEQ ID No. 18), the other with the oligonucleotides Sq3895 (SEQ ID No. 19) and VACla3'. The fragments derived from these PCRs are 162 and 118 bp respectively. A third PCR was performed on a mixture of these two fragments, after their purification, by means of the oligonucleotides VACla5' and VACla3'. The 271 bp fragment obtained was cloned into the plasmid pCRII (Invitrogen) and its sequence verified over 254 bp (SEQ ID No. 24). The resulting plasmid was called pXL2407.

11. Construction of the plasmids pXL2408 and pXL2409

The plasmids pXL2408 and pXL2409 are eukaryotic expression vectors containing a VA RNA$_f$ modified by insertion of a 33 nucleotide sequence respectively complementary to the sequences +44/+76 and +441/+473 of the cDNA encoding human apoA-II. Furthermore, they contain the sequences encoding resistance to neomycin and kanamycin.

They were constructed in the following manner:
digestion of the plasmids pXL2405 and pXL2406 with ClaI, and then,
insertion of the ClaI—ClaI fragments from each plasmid, containing the modified VA RNA$_f$'s, into the vector pVV2, previously linearized with ClaI. The plasmids were designated pXL2408 and pXL2409 respectively.

C2. Functionality of the antisense RNAs

The vectors expressing an antisense RNA (pXL2270, pXL2271, pXL2404, pXL2408, pXL2409) were tested:
for their expression, after transient transfection into COS-1 cells,
for their functionality by transient expression in the same cells, after cotransfection with pXL2403,
for their functionality by generation of stably transfected cell lines 293.

1. Expression of the antisense RNAs

The vectors expressing the antisense RNAs were introduced into the COS-1 cells by electroporation. 48 hours after transfection, the total RNAs were extracted from the cells. The presence of antisense messenger RNAs was detected by the Northern blot technique. For that, the total RNAs were loaded onto agarose gel in the presence of formaldehyde and then transferred onto nylon membrane. The membrane was hybridized with a probe radiolabelled with $^{32}$phosphorus. For the expression of the modified VA RNA$_f$'s, this probe was either the cDNA encoding VA RNA$_f$, or the oligonucleotide Sq4112 (SEQ ID No. 20). For the expression of the complete antisense RNA, this probe was either the cDNA encoding human apoA-II, or the oligonucleotide Sq3320 (SEQ ID No. 9). The specific binding of the probe onto the RNAs of the membrane was revealed after autoradiography at −80° C. The results obtained show that, for all the constructs tested, the expression of the antisense transcripts can be detected.

2. Expression of apolipoprotein A-II

The plasmid pXL2403 was tested for its functionality, by expression in COS-1 cells. For that, the plasmid was introduced into the cells by electroporation. Two days after the transfection, the total RNAs were extracted from the cells and the presence of messenger RNA encoding apoA-II was detected by the Northern blot technique, with the aid of specific probes: either the cDNA encoding human apoA-II, or the oligonucleotide Sq3319 (SEQ ID No. 8). On the other hand, the cellular supernatants were recovered and tested for their apoA-II content by an ELISA test. For the ELISA test, a monoclonal antibody directed against apoA-II (10 μg/ml in carbonate buffer, pH=9.6) was attached to the wells of an Immulon II plate (Dynatech), by overnight incubation at +4° C. The wells were then saturated for one hour at 37° C. with bovine serum albumin (diluted to 2% in PBS buffer of pH=7.4). The pure or diluted (dilution in PBS-2% BSA) cellular supernatants were deposited in the wells and incubated for one hour at 37° C. The revealing was then carried out by (i) incubating the wells, for one hour at 37° C., with a mixture of anti-apoA-II monoclonal antibodies covalently bound to peroxidase, (ii) incubating, in the dark, in the presence of the TMB reagent and (iii) spectrophotometric reading at a wavelength of 630 nm. The results obtained show that the expression of apolipoprotein A-II can be detected.

3. Generation of cell lines 293 stably expressing the antisense RNAs

The vectors expressing the antisense RNAs were introduced into the cells 293 by the technique of transfection in the presence of calcium phosphate. A vector carrying the neomycin resistance gene was introduced together with the vector pXL2404. The selection of the clones having received the antisense vectors was performed by culturing the cells in the presence of G418 (400 μg/ml). The clones were then characterized and selected for the presence of cDNA encoding the antisense RNA (PCR) and of the antisense transcript (Northern blotting). The selected stable lines as well as the parental line 293 were then transfected by the plasmid pXL2403. 48 hours after the transfection, the cellular supernatants were recovered and tested for their apoA-II content by an ELISA test (cf. 2. above).

C3. Preparation of the recombinant adenoviruses

The plasmids prepared in C1 were then linearized and cotransfected for recombination with a deficient adenoviral vector, into the helper cells (line 293) supplying in trans the functions encoded by the adenovirus E1 regions (E1A and E11B), according to the procedure described in Example A3.

Example D
Construction of a defective recombinant adenovirus containing the apolipoprotein E gene
D1. Construction of the plasmid pXL2335

This plasmid contains the cDNA for isoform 3 of ApoE under the control of the RSV promoter.

Figure 10:
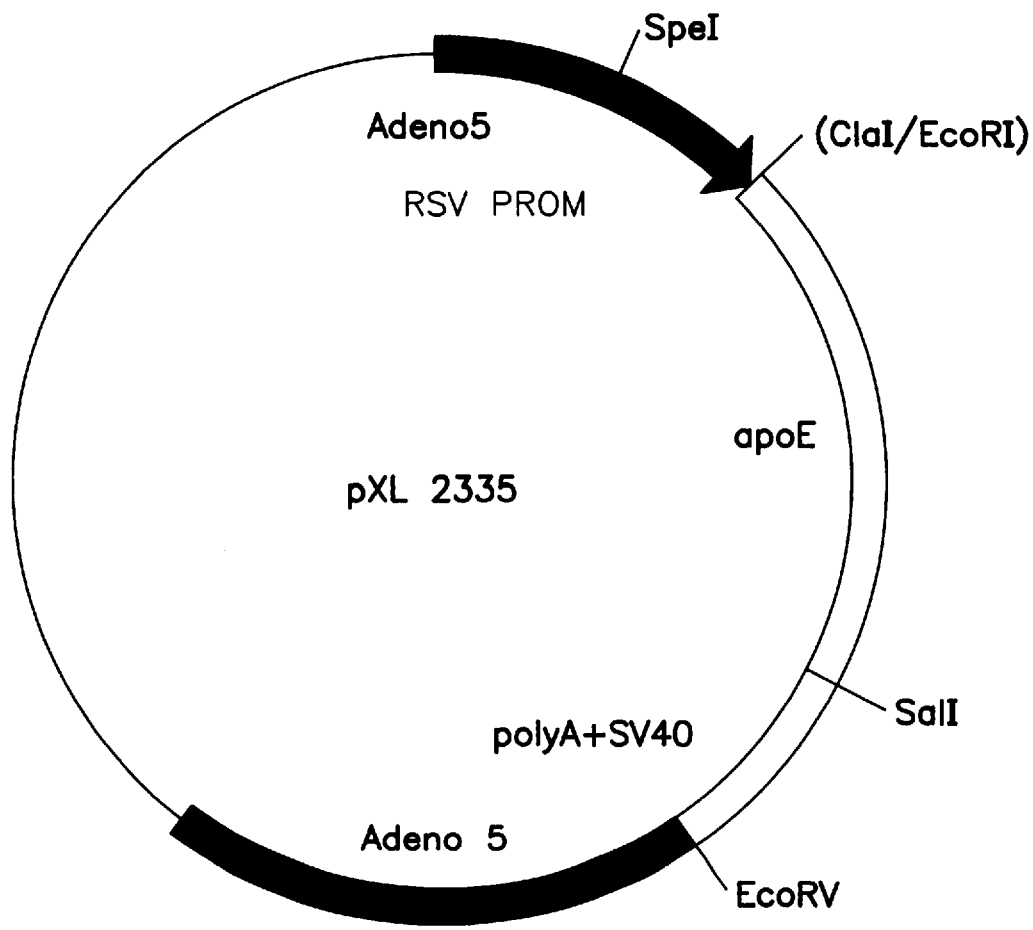
FIG. 10: Representation of the plasmid pXL2335.

It was constructed by cloning the cDNA contained at the SmaI site of a plasmid pGEM3, removed by an EcoRI cut, filled with T4 polymerase and a second SalI cut and inserted into the plasmid pXL2244 opened with ClaI, filled with Klenow and recut with SalI (FIG. 10).

D2. Preparation of the recombinant adenoviruses

The plasmid pXL2335, prepared in $D_1$, is then linearized and cotransfected for recombination with a deficient adenoviral vector, into the helper cells (line 293) supplying in trans the functions encoded by the adenovirus E1 regions (E1A and E11B), according to the procedure described in Example A3.

---

We claim:

1. A replication defective recombinant adenovirus comprising an inserted gene encoding human apolipoprotein AI or a natural variant thereof, wherein the inserted gene is under the control of a sequence permitting expression of the gene in a cell.

2. The adenovirus according to claim 1, wherein said adenovirus is a type Ad 5 adenovirus.

3. The adenovirus according to claim 1, wherein the sequence is a CMV or RSV promoter.

4. The adenovirus according to claim 1, wherein the inserted gene comprises a signal sequence.

5. A pharmaceutical composition comprising a defective recombinant adenovirus according to claim 1.

6. A pharmaceutical composition according to claim 5, in injectable form.

7. A pharmaceutical composition according to claim 5, comprising between $10^4$ and $10^{14}$ pfu/ml of defective recombinant adenovirus.

8. The adenovirus according to claim 1, wherein the inserted gene encodes an apolipoprotein AI variant having a cysteine in position 173.

9. A method for the treatment of atherosclerosis comprising administering to an animal an adenovirus of claim 1, wherein the gene encoding apolipoprotein A1 or a natural variant thereof is expressed at a level effective to inhibit arterial lipid deposition.

10. A pharmaceutical composition according to claim 7, comprising between $10^6$ to $10^{10}$ pfu/ml of defective recombinant adenovirus.

11. The method according to claim 9, wherein the animal is a human.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq1851"

( i i i ) HYPOTHETICAL: NO ( i v ) ANTI-SENSE: NO ( x i ) SEQUENCE DESCRIPTION: SEQ ID NO:1:

```
TCTGGCAGCA AGATGAAACC CCCCAGAGCC CCTGGGATCG AGTGAAGGAC CTGGCCACTG        60
T                                                                       61
```

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq1852"

( i i i ) HYPOTHETICAL: NO ( i v ) ANTI-SENSE: NO ( x i ) SEQUENCE DESCRIPTION: SEQ ID NO:2:

```
CGCGGATCCG CGCAGCTTCT CTTGCAGCTC GTG                                    33
```

( 2 ) INFORMATION FOR SEQ ID NO:3:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq1849"

( i i i ) HYPOTHETICAL: NO ( i v ) ANTI-SENSE: NO ( x i ) SEQUENCE DESCRIPTION: SEQ ID NO:3:

```
GGGGAAGCTT ATGAAAGCTG CGGTGCTGAC CTTGGCCGTG CTCTTCCTGA CGGGG           55
```

( 2 ) INFORMATION FOR SEQ ID NO:4:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq1850"

( i i i ) HYPOTHETICAL: NO ( i v ) ANTI-SENSE: NO ( x i ) SEQUENCE DESCRIPTION: SEQ ID NO:4:

GGGGGGGGTT CATCTTGCTG CCAGAAATGC CGAGCCTGGC TCCCCGTCAG GAAGACGACG     60

G     61

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq3561"

( i i i ) HYPOTHETICAL: NO ( i v ) ANTI-SENSE: NO ( x i ) SEQUENCE DESCRIPTION: SEQ ID NO:5:

TGCTGACCTT GGCCGTGCTC     20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq3571"

( i i i ) HYPOTHETICAL: NO ( i v ) ANTI-SENSE: NO ( x i ) SEQUENCE DESCRIPTION: SEQ ID NO:6:

CGCAGCGGCT CCACCTTCTG     20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq3570"

( i i i ) HYPOTHETICAL: NO ( i v ) ANTI-SENSE: NO ( x i ) SEQUENCE DESCRIPTION: SEQ ID NO:7:

GGACAGAGCT GATCCTTGAA                                                                            20

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq3319"

( i i i ) HYPOTHETICAL: NO ( i v ) ANTI-SENSE: NO ( x i ) SEQUENCE DESCRIPTION: SEQ ID NO:8:

GGATTCATTC AGCATTTATT GTAGCAAAG                                                                  29

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq3320"

( i i i ) HYPOTHETICAL: NO ( i v ) ANTI-SENSE: NO ( x i ) SEQUENCE DESCRIPTION: SEQ ID NO:9:

AGGCACAGAC ACCAAGGACA GAGACGCTGG                                                                 30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq3364"

( i i i ) HYPOTHETICAL: NO ( i v ) ANTI-SENSE: NO ( x i ) SEQUENCE DESCRIPTION: SEQ ID NO:10:

CTCAAGAAGT TAACCTGGTG AGGAGTAGCA                                                                 30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide sq3369"

( i i i ) HYPOTHETICAL: NO ( i v ) ANTI-SENSE: NO ( x i ) SEQUENCE DESCRIPTION: SEQ ID NO:11:

TGCTACTCCT CACCAGGTTA ACTTCTTGAG                                               30

( 2 ) INFORMATION FOR SEQ ID NO:12:

( i ) SEQUENCE CHARACTERISTICS:
        ( A ) LENGTH: 473 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:12:

GGATTCATTC AGCATTTATT GTAGCAAAGA GTGGGTAGGG ACAGGAGCTC TAGGACTGGC            60
CAGTGGGTGT TCTAGAGGCC AGCTGGGGTT GGAAGACAAT GGTCTGGACA CTTCACTGGG           120
TGGCAGGCTG TGTTCCAAGT TCCACGAAAT AGCTCAAGAA GTTAACCAGT TCCGTTCCAG           180
CCTTCTTGAT CAGGGGTGTC AGCTGCTCCT TTGACTTTTC AAAGTAAGAC TTGGCCTCGG           240
CCTGAAGCTC TGGGCTCTTG ACCTTCTCCA TCAGGTCCTT GCCATAGTCA GTCACGGTCT           300
GGAAGTACTG AGAAACCAGG CTCTCCACAC ATGGCTCCTT TGCCTGTCTC CGAACCAAAG           360
CTCCTTCAAG GCTGCAGATG GTGAGGAGTA GCACAGTTGC TGCGAGCAGC TTCATGTTGG           420
TAACAGTGGG GAGGGCGGCC TAGCCAGCGT CTCTGTCCTT GGTGTCTGTG CCT                  473

( 2 ) INFORMATION FOR SEQ ID NO:13:

( i ) SEQUENCE CHARACTERISTICS:
        ( A ) LENGTH: 262 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:13:

GGATTCATTC AGCATTTATT GTAGCAAAGA GTGGGTAGGG ACAGGAGCTC TAGGACTGGC            60
CAGTGGGTGT TCTAGAGGCC AGCTGGGGTT GGAAGACAAT GGTCTGGACA CTTCACTGGG           120
TGGCAGGCTG TGTTCCAAGT TCCACGAAAT AGCTCAAGAA GTTAACCTGG TGAGGAGTAG           180
CACAGTTGCT GCGAGCAGCT TCATGTTGGT AACAGTGGGG AGGGCGGCCT AGCCAGCGTC           240
TCTGTCCTTG GTGTCTGTGC CT                                                    262

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide VACIa5'"

( i i i ) HYPOTHETICAL: NO ( i v ) ANTI-SENSE: NO ( x i ) SEQUENCE DESCRIPTION: SEQ ID NO:14:

GTTATCGATC TAGACCGTGC AAAAGGAGAG CC  32

( 2 ) INFORMATION FOR SEQ ID NO:15:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide VACla3'"

( i i i ) HYPOTHETICAL: NO ( i v ) ANTI-SENSE: NO ( x i ) SEQUENCE DESCRIPTION: SEQ ID NO:15:

CTTCCAGGCG CGGCGGCTGC TGCGATCGAT TTT  33

( 2 ) INFORMATION FOR SEQ ID NO:16:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide Sq3892"

( i i i ) HYPOTHETICAL: NO ( i v ) ANTI-SENSE: NO ( x i ) SEQUENCE DESCRIPTION: SEQ ID NO:16:

GCCGTGATCC ATGCGGTTTG CTGCGAGCAG CTTCATGTT  39

( 2 ) INFORMATION FOR SEQ ID NO:17:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide Sq3893"

( i i i ) HYPOTHETICAL: NO ( i v ) ANTI-SENSE: NO ( x i ) SEQUENCE DESCRIPTION: SEQ ID NO:17:

CTTCATGTTG GTAACAGTGG GACCGCCCGC GTGTCGAAC  39

( 2 ) INFORMATION FOR SEQ ID NO:18:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide Sq3894"

( i i i ) HYPOTHETICAL: NO ( i v ) ANTI-SENSE: NO ( x i ) SEQUENCE DESCRIPTION: SEQ ID NO:18:

GCCGTGATCC ATGCGGTTGG ATTCATTCAG CATTTATTG                                                       39

( 2 ) INFORMATION FOR SEQ ID NO:19:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide Sq3895"

( i i i ) HYPOTHETICAL: NO ( i v ) ANTI-SENSE: NO ( x i ) SEQUENCE DESCRIPTION: SEQ ID NO:19:

CATTTATTGT AGCAAAGAGT GACCGCCGC GTGTCGAAC                                                        39

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Oligonucleotide Sq4112"

( i i i ) HYPOTHETICAL: NO ( i v ) ANTI-SENSE: NO ( x i ) SEQUENCE DESCRIPTION: SEQ ID NO:20:

AAAAGGAGCG CTCCCCCGTT GTCTGACGTC                                                                 30

( 2 ) INFORMATION FOR SEQ ID NO:21:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Anti- apoAII partial
            antisense, complementary to the sequence +44/+76."

( i i i ) HYPOTHETICAL: NO ( i v ) ANTI-SENSE: YES ( x i ) SEQUENCE DESCRIPTION: SEQ ID NO:21:

TGCTGCGAGC AGCTTCATGT TGGTAACAGT GGG                                                             33

( 2 ) INFORMATION FOR SEQ ID NO:22:

( i ) SEQUENCE CHARACTERISTICS:
        ( A ) LENGTH: 254 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Anti- apoAII partial
            antisense, cloned into pXL2406."

( i i i ) HYPOTHETICAL: NO ( i v ) ANTI-SENSE: YES (xi) SEQUENCE DESCRIPTION: SEQ ID NO:22:

| | | | | | | |
|---|---|---|---|---|---|---|
| TCTAGACCGT | GCAAAAGGAG | AGCCTGTAAG | CGGGCACTCT | TCCGTGGTCT | GGTGGATAAA | 60 |
| TTCGCAAGGG | TATCATGGCG | GACGACCGGG | GTTCGAACCC | CGGATCCGGC | CGTCCGCCGT | 120 |
| GATCCATGCG | GTTTGCTGCG | AGCAGCTTCA | TGTTGGTAAC | AGTGGGACCG | CCCGCGTGTC | 180 |
| GAACCCAGGT | GTGCGACGTC | AGACAACGGG | GGAGCGCTCC | TTTTGGCTTC | CTTCCAGGCG | 240 |
| CGGCGGCTGC | TGCG | | | | | 254 |

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Anti- apoAII partial
            antisense, complementary to the sequence +441/+473."

(iii) HYPOTHETICAL: NO (iv) ANTI-SENSE: YES (xi) SEQUENCE DESCRIPTION: SEQ ID NO:23:

| | | | |
|---|---|---|---|
| GGATTCATTC | AGCATTTATT | GTAGCAAAGA | GTG | 33 |

(2) INFORMATION FOR SEQ ID NO:24:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Anti- apoAII partial
            antisense, cloned into pXL2407."

(iii) HYPOTHETICAL: NO (iv) ANTI-SENSE: YES (xi) SEQUENCE DESCRIPTION: SEQ ID NO:24:

| | | | | | | |
|---|---|---|---|---|---|---|
| TCTAGACCGT | GCAAAAGGAG | AGCCTGTAAG | CGGGCACTCT | TCCGTGGTCT | GGTGGATAAA | 60 |
| TTCGCAAGGG | TATCATGGCG | GACGACCGGG | GTTCGAACCC | CGGATCCGGC | CGTCCGCCGT | 120 |
| GATCCATGCG | GTTGGATTCA | TTCAGCATTT | ATTGTAGCAA | AGAGTGACCG | CCCGCGTGTC | 180 |
| GAACCCAGGT | GTGCGACGTC | AGACAACGGG | GGAGCGCTCC | TTTTGGCTTC | CTTCCAGGCG | 240 |
| CGGCGGCTGC | TGCG | | | | | 254 |